United States Patent [19]

Hägele

[11] Patent Number: 4,572,807
[45] Date of Patent: Feb. 25, 1986

[54] OLIGOPHOSPHONIC ACIDS, OLIGOPHOSPHINIC ACIDS, AND PROCESS OF PREPARATION

[75] Inventor: Gerhard Hägele, Hilden, Fed. Rep. of Germany

[73] Assignee: Henkel Kommanditgesellschaft auf Aktien, Düsseldorf-Holthausen, Fed. Rep. of Germany

[21] Appl. No.: 357,489

[22] Filed: Mar. 12, 1982

[30] Foreign Application Priority Data

Mar. 21, 1981 [DE] Fed. Rep. of Germany ....... 3111152

[51] Int. Cl.$^4$ ............................. C07F 9/30; C07F 9/38
[52] U.S. Cl. ............................. 260/932; 260/502.4 P; 260/970
[58] Field of Search .......... 260/932, 970, 932, 502.4 P

[56] References Cited

U.S. PATENT DOCUMENTS

| 2,651,656 | 9/1953 | Ladd et al. ........................... 260/970 |
| 3,471,552 | 10/1969 | Budnick ........................ 260/502.4 P |
| 3,501,555 | 3/1970 | Frank et al. ........................ 260/932 |
| 3,743,688 | 7/1973 | Nicholson et al. ................... 260/932 |
| 3,808,273 | 4/1974 | Kerst ................................... 260/932 |

FOREIGN PATENT DOCUMENTS 0061106 9/1982 European Pat. Off. ............ 260/932

OTHER PUBLICATIONS

Tetrahedron, vol. 26, No. 23, Dec. 1970, pp. 5529–5534.
Journal of the Chemical Society, Jun. 1963, pp. 3351–3360.

Primary Examiner—Anton H. Sutto
Attorney, Agent, or Firm—Hammond & Littell, Weissenberger & Dippert

[57] ABSTRACT

This invention relates to a process for preparing oligophosphonic or oligophosphinic acids or esters or salts thereof which comprises reacting an alkali metal ester of phosphorous acid or an alkali metal ester of arylphosphonous or alkylphosphonous acid with an olefin polyhalide and, optionally, saponifying the resultant product.

46 Claims, No Drawings

OLIGOPHOSPHONIC ACIDS, OLIGOPHOSPHINIC ACIDS, AND PROCESS OF PREPARATION

FIELD OF THE INVENTION

This invention relates to oligophosphonic acids and oligophosphinic acids. More specifically, this invention relates to oligophosphonic acids and oligophosphinic acids, to salts and esters thereof, and to the preparation thereof.

BACKGROUND OF THE INVENTION

The preparation of alkylphosphonic acid dialkyl esters of the formula $RP(O)(OR')_2$ by the reaction of alkylhalides of the formula RX with dialkylphosphite salts of the formula $(R'O)_2POMe$ in alcoholic solution of the formula R'OH according to the following reaction scheme:

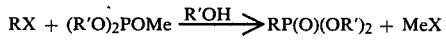

has been known since the turn of the century and is known as the "Michaelis-Becker" reaction. See, for example, Houben-Weyl "Methoden der organischen Chemie", 4th edition (1963), Vol. 12, pages 446 et seq. Preferably R represents n-alkyl in this reaction; the yields are lower with secondary and tertiary alkylhalides. The X group is preferably chlorine, but it may also be bromine or iodine. For technical reactions, R' is preferably ethyl or n-butyl, and Me is preferably sodium. Furthermore, while the reaction is preferably carried out in alcohols, ethers or aromatic compounds may optionally be used as solvents.

The principle of the Michaelis-Becker reaction has also been applied to the synthesis of oligophosphonic acids. For example, when allylbromide ($CH_2=CH-CH_2Br$) is used, substitution takes place, followed by the addition of sodium dialkylphosphite. Finally, the diphosphonic acid ester of the formula

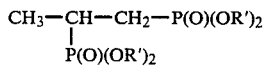

is obtained. The conversion of α-bromostyrene to the ester of the formula

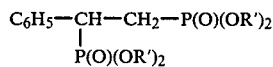

proceeds in a similar manner.

No mention is made in the literature about successful conversions of polyhalogenated olefins under the conditions of the Michaelis-Becker reaction.

U.S. Pat. No. 3,471,552 discloses a process by which methane polyhalides such as chloroform, carbon tetrachloride, bromoform, or carbon tetrabromide are reacted with sodium dialkylphosphite, a mixture of xylene and tetrahydrofuran being used as solvents. Methane oligophosphonic acid esters are reportedly formed. However, testing of the data disclosed shows that the reactions do not proceed as smoothly as stated. Side reactions to the planned reactions are dominant, as can be demonstrated with nuclear resonance spectra. It has to be concluded that the reactions of chloroform and, especially, carbon tetrachloride are described incorrectly in this patent.

When the reaction of a polyhalogenated olefin selected from the group consisting of vinylidene chloride ($CH_2=CCl_2$), trichloroethylene ($CHCl=CCl_2$), and tetrachloroethylene ($CCl_2=CCl_2$) with sodium diethylphosphite in ethanol is attempted, the following observation is made: Hardly any conversion takes place in the case of vinylidene chloride and trichloroethylene, and tetrachloroethylene converts quantitatively into the triethyl phosphate. Polyphosphonic acid compounds are not produced.

OBJECTS OF THE INVENTION

It is an object of the invention to provide novel oligophosphonic acids and oligophosphinic acids.

It is also an object of the invention to provide salts and esters of said oligiphosphonic acids and oligophosphinic acids.

It is a further object of the invention to provide novel phosphonic acid and phosphinic acid derivatives.

It is a yet further object of the invention to provide methods of preparing said oligophosphonic acids, oligophosphinic acids, and derivatives thereof.

These and other objects of the invention will become more apparent in the discussion below.

DETAILED DESCRIPTION OF THE INVENTION

Applicant's invention is directed to a novel, effective, and broadly applicable method for preparing polyphosphonic acids and related compounds with which known and, in particular, novel compounds can be readily prepared. The basis for the invention is Applicant's surprising observation concerning the selection of certain reactants, particularly the organic polyhalide compounds, for the reaction system described below.

More specifically, the invention is directed to a method for the preparation of oligophosphonic acids or oligophosphinic acids, their salts, and/or their esters by the reaction of organic halogen compounds with diesters of phosphorous acid or with esters of alkyl- or arylphosphonous acids. The method is characterized by the fact that olefin polyhalides with a terminal double bond and having the general formula

wherein $R^1$ and $R^2$, which may be the same or different, each represent a hydrogen or halogen atom or a hydrocarbon radical and Hal represents a halogen atom, are reacted, with exchange of halogens located at the double bond and simultaneous saturation of the double bond, with alkali metal salts of diesters of phosphorous acid or alkali metal salts of esters of alkyl- or arylphosphonous acids and, optionally, the reaction products formed are saponified to form the free phosphonic or phosphinic acids or their salts.

The conversion of the reactants according to the invention preferably proceeds in the presence of selected solvents. Liquid ethers and tertiary amines have been found to be especially suitable as solvents at the reaction temperature. The ethers as well as the tertiary bases may have cyclic structure or open-chain structure for this purpose. A very specially preferred solvent according to the intent of the invention is tetrahydrofuran, which yields especially low-viscosity solutions even with comparatively high contents of reactants, particularly with high contents of the salts of phosphorus-containing esters. Another very suitable ether solvent is methyl-tert.butyl-ether. However, other cyclic or noncyclic ethers, for example, dioxane or a polyglyme, can be used. A suitable cyclic tertiary base is pyridine, for example. But again, as in the case of the ethers, open-chain tertiary bases may be used, provided that they are liquid under the reaction conditions and consequently can serve as solvent or reaction medium.

It has been observed that the phosphite anion serves not only as a halogen-abstracting base in the presence of these media, but that the phosphite anion can substitute for halogen directly and can produce P-C bonds under these conditions. In addition, the phosphite anion adds to, that is, saturates, the unsaturated systems. Oligophosphonic acid esters or the corresponding acids become accessible with a practically single-step procedure in this manner. Comparable reaction mechanisms lead to oligophosphinic acids or their esters or salts when alkali metal salts of (mono)esters of alkyl- or arylphosphonous acids are used. The class of organic alkyl- or arylphosphinyl compounds (phosphinic acids) is known as such and described, for example, by the alkan-1,1-bis-(alkylphosphinyl compounds) in *Z. anorg. allg. Chemie.*, Vol. 399: 1-6 (1973). For example, the preparation of 1-hydroxyalkan-1,1-bis-(alkylphosphinic acids) as structural analogs of the 1-hydroxy-alkan-1,1-diphosphonic acids is disclosed. The description below is based mainly on the description of the oligophosphonic acid compounds or their preparation, but it is also applicable to the corresponding oligophosphinic acids and their derivatives, unless stated otherwise.

The olefin polyhalides used as starting materials according to the invention correspond to the compounds of Formula I. The terminal double bond and the perhalogenation at the terminal carbon atom are characteristic. In accordance with the invention, this double bond of the starting material disappears in the reaction in favor of a saturated C—C bond at the same place in the molecule.

The substitution of the second carbon atom involved in the double bond of the compounds of Formula I permits a broad variation in the process according to the invention. As mentioned above, the radicals $R^1$ and $R^2$, which may be the same or different, may each represent a hydrogen or halogen atom or a hydrocarbon radical, the term "hydrocarbon" having the broad significance described below. Characteristic substances or substance classes for this starting material comprise the following: (1) $R^1$ and $R^2$ represent hydrogen (vinylidene halide); (2) one of the radicals represents hydrogen, the other halogen (trihalogen ethylene); (3) both radicals represent halogen (tetrahalogen ethylene); (4) one of the radicals is a hydrocarbon radical, the other radical is either hydrogen or halogen; and (5) both radicals are identical or different hydrocarbon radicals. As shall be demonstrated later, among other things, the respective choice of the specific starting materials influence the constitution of the oligophosphonic or oligophosphinic acids formed.

The olefin polyhalides of Formula I can be used with halogen substituents, and the respective halogen atoms present in the starting material may be identical or different. Even the two "Hal" moieties may represent two different halogen atoms.

Usually fluorine-substituted olefins are the least interesting. Not only are they the slowest reacting, but special consideration must be given to the fact that physiologically questionable compounds may be formed that contain fluorine and phosphonic or phosphinic acid radicals simultaneously. The most important halogens of the starting material are chlorine and/or bromine, and exclusively chlorinated starting materials can have special significance, particularly for technical application.

The choice of the respective halogen substitution can be significant for the choice of the remaining reaction conditions. Generally, the following rules apply to this situation: The reactivity of the olefin halide increases in the sequence $F<Cl<Br<I$. Also, the activity of the olefin halide increases with the increasing number of halogen atoms in the starting material. Consequently, optimal conversion conditions can be selected for a given case, in consideration with other process variables to be described below.

When $R^1$ and/or $R^2$ represent a hydrocarbon radical, this term may be given broad interpretation according to the invention. The term encompasses virtually all saturated, unsaturated, or aromatic hydrocarbon radicals, which may be linear, branched, or cyclic, provided that there are no restrictions or objections due to steric reasons, such as steric hindrance. The hydrocarbon radicals may also contain heteroatoms, and particular heterocyclic radicals may consequently be present as well. Suitable heteroatoms especially include N, O, S, and/or P, the presence of from 1 to 3 of such heteroatoms in the particular radical being preferred. The number of carbon atoms in $R^1$ and $R^2$ is theoretically not subject to any limitation. For practical reasons, the number of carbon atoms per radical is usually not more than 25 and preferably not more than 20. Comparatively shorter $R^1$ and $R^2$ hydrocarbon radicals of, for example, up to 10 carbon atoms are preferred, and radicals of only up to 6 carbon atoms are especially preferred. The specific selection of the radicals $R^1$ and $R^2$ in the respective starting material is determined by the desired structure of the oligophosphonic or oligophosphinic acid.

The radicals $R^1$ and $R^2$ described above may also be themselves substituted or carry functional groups, provided that the substituents or functional groups cannot themselves enter in an undesirable manner into interactions with the other reactants of the reaction according to the invention. The knowledge of the state of the art on the subject applies to each individual case. However, it may be absolutely desirable within the scope of the invention that reactions also involving such substituents or reactive groups on $R^1$ and/or $R^2$ do take place under the process conditions used according to the invention, with the alkali metal salts of diesters of phosphorous acid or respective salts of esters of alkyl- or arylphosphorous acids. For example, the possibility that the introduction of phosphonic acid or phosphinic acid groups takes place also at additional places on the molecule used can be provided by suitable halogen substitution of $R^1$ and/or $R^2$. In a special case significant according to the invention, at least one of $R^1$ and $R^2$ carries a terminal double bond that is halogenated at least at its terminal carbon atom. Consequently, the starting compound in this case has the reactive group represented in Formula I at least twice. A representative example comprises halogenated butadiene derivatives, particularly perhalogenated butadiene, corresponding isoprene derivatives, and comparable compounds. At least terminally perhalogenated α,ω-diolefins can generally meet this condition for starting materials according to the invention. It is apparent that a large number of new polyphosphonic acid or polyphosphinic acid compounds, which offer properties interesting for many purposes, become accessible according to the procedure described.

Finally, the given constitution of the olefin polyhalide used affects the maximum number of phosphonic acid or phosphinic acid groups that can be introduced. Accordingly, at least two, but generally three or four phosphonic or phosphinic acid groups are present in the end product, per reaction unit based upon the compound of Formula I. Vinylidene chloride, for example, yields 1,1,2-ethane-trisphosphonic acid, and tetrachloroethylene yields the novel compound 1,1,2,2-ethane-tetrakisphosphonic acid. Depending on the choice of reaction conditions, trichloroethylene can yield 1,1,2-tris acid or 1,1,2,2-tetrakis acid. Starting compounds of Formula I in which one of $R^1$ and $R^2$ represents a hydrocarbon radical generally lead to trisphosphonic acid products.

The respective structure of the olefin halides of Formula I used can also influence the reactivity of the conversion according to the invention. Least reactive, in general, are the starting compounds of Formula I substituted with two hydrocarbon radicals. The corresponding compounds with only one hydrocarbon radical follow; then, the reactivity increases with the increasing halogen content, for example, in the direction vinylidene chloride < trichloroethylene < tetrachloroethylene.

The olefin polyhalides of Formula I are used together with the esters of phosphorous acid for the introduction of phosphonic acid groups. These latter reactants are advantageously used in the form of their alkali metal salts, the sodium salt being the most important alkali metal salt. The compounds can be expressed by the formula

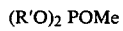

in which Me is an alkali metal, especially sodium, and R' a hydrocarbon radical, especially a linear or branched alkyl radical. However, tert.alkyl radicals are generally undesirable. The alkyl radical R' may contain, for example, up to 25 carbon atoms, preferably up to 20 carbon atoms. Working with shorter-chain lower-membered alkyl radicals, for example, those of up to 12, especially up to 8, carbon atoms, is particularly preferred.

The choice of the respective alkyl radicals—or those of the given ester groupings in the dialkylphosphite salts—may in turn influence, for example, the reactivity of the system. The most reactive phosphite esters are the lower alkyl esters with especially from 2 to 5 carbon atoms in the respective alkyl radical. Sodium diethylphosphite or the corresponding n-butyl compound, can become significant when the free polyphosphonic acids or their salts are required instead of polyphosphonic acid esters. When, after the introduction of the phosphonic acid ester groupings into the compounds of Formula I, saponification to the free polyphosphonic acid takes place, the original nature of the ester-forming alcohol component has become unimportant in the saponification product obtained. However, when the preservation of the ester groupings is required, then it must be considered that, for example, the isopropyl esters are less reactive than the ethyl esters but still more reactive than the isooctyl esters.

The dialkylphosphite salt needed as a reactant for the method according to the invention can be obtained by a known method, for example, by reaction of sodium hydride with the respective dialkylphosphite, using an inert protective gas, for example, dry nitrogen, to exclude the action of atmospheric oxygen and particularly moisture. Especially suitable as dialkylphosphites according to the invention are phosphorous acid dialkyl esters with from 1 to 8 carbon atoms in the linear or branched alkyl radical.

Corresponding salts of esters of alkyl- or arylphosphonous acids can be used instead of the dialkylphosphites. These reactants are represented by the formula

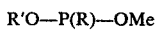

wherein R' and Me are as defined above and R represents an alkyl or aryl. Here, Me is especially sodium and R' is preferably a linear or branched alkyl radical with from 1 to 8 carbon atoms. With respect to R, a phenyl radical is particularly suitable as an aryl radical, and important among alkyl radicals are lower alkyl radicals with from 1 to 5, preferably from 1 to 3 carbon atoms. Such alkyl- or arylphosphonous acids can also be prepared by known methods. See, for example, the reference to Z. anorg. allg. Chemie mentioned above as well as German published applications (DE-OS) Nos. 21 53 998 and 21 53 999, incorporated herein by reference. The preparation of a fresh solution from the respective salts of the phosphorus-containing reactants of both groups described above and the immediate addition to the subsequent reaction, is preferable.

Another important part of the process according to the invention is the simultaneous use, under liquid reaction conditions of the reaction additives mentioned initially, that is, the cyclic or open-chain ethers or the corresponding tertiary nitrogen bases. Tetrahydrofuran or methyl tert.butyl ether are especially suitable solvents according to the invention. Easily flowing, low-viscosity solutions of the salts of the phosphorus containing esters can be prepared with tetrahydrofuran. The desired formation of the P-C bonding is obtained in the presence of tetrahydrofuran or the other mentioned solvents, whereas parallel trials with a large number of other solvents did not produce this result.

For a particular case, it may be advantageous to add both reactants dissolved in, for example, tetrahydrofuran, to the reaction. The preparation of the dialkylphosphite salts, for example, can take place immediately in tetrahydrofuran.

For the reaction according to the invention, the reactants are preferably used in the proper quantitative proportions so that all halogen atoms located at double bonds according to Formula I can be exchanged against phosphonic acid or phosphinic acid ester groups. Also preferred for a particular case is the use of the alkali metal salts of phosphorus-containing esters or diesters in an excess beyond the amount stoichiometrically needed for the mere exchange of the halogen for phosphonic or phosphinic acid groups. The work is preferably performed with an excess of at least approximately 1 mol of alkali metal salt per mol of olefin polyhalide, this "excess" being given by the mathematical comparison of the number of halogen atoms located at double bonds, on the one hand, and alkali metal atoms on the other hand. An excess of 1 mol of alkali metal salt per mol of olefin halide can be particularly advantageous.

The reason for this working with the excess of the phosphorus-containing reaction component is that the reaction course of the conversion according to the invention is apparently not generally limited to a simple substitution in the sense of the Michaelis-Becker reaction. On the contrary, a release of hydrogen halide (HCl) or halogen (Cl$_2$) takes place in an intermediary step—dependent upon the starting compound and possibly reaction conditions—under the influence of the phosphorus-containing reactants. The acetylene bond formed in this manner enters into the reaction. The course of the reaction using vinylidene chloride, trichloroethylene, and tetrachloroethylene, as examples, can be shown with the following equations (P$^+$ = P(O)-(OR')$_2$):

I. Vinylidene chloride

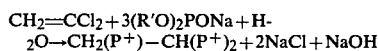

$$CH_2=CCl_2+3(R'O)_2PONa+H_2O \rightarrow CH_2(P^+)-CH(P^+)_2+2NaCl+NaOH$$

II. Tetrachloroethylene

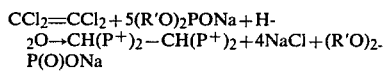

$$CCl_2=CCl_2+5(R'O)_2PONa+H_2O \rightarrow CH(P^+)_2-CH(P^+)_2+4NaCl+(R'O)_2P(O)ONa$$

III. The reactions of trichloroethylene can be steered in two directions (as is described below):

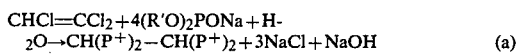

$$CHCl=CCl_2+4(R'O)_2PONa+H_2O \rightarrow CH(P^+)_2-CH(P^+)_2+3NaCl+NaOH \quad (a)$$

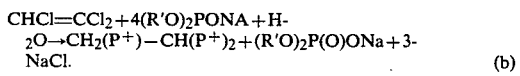

$$CHCl=CCl_2+4(R'O)_2PONA+H_2O \rightarrow CH_2(P^+)-CH(P^+)_2+(R'O)_2P(O)ONa+3NaCl. \quad (b)$$

A release of HCl presumably takes place in an intermediary step in case (a), and the release of Cl$_2$ probably takes place in case (b).

A steering of the course of the reaction in the direction (a) or (b) as set forth above is accomplished as follows: First, the choice of the addition sequence can be of crucial importance. When the phosphorus-containing reactant, for example, dialkylphosphite salt, is placed in the vessel and trichloroethylene is added, the formation of ethane triphosphonic acid is favored. On the other hand, when trichlorethylene is placed in the vessel and the phosphorus-containing reactant—for example, dialkylphosphite salt—is added to this bath, the formation of ethane-tetrakisphosphonic acid is favored. In addition, the nature of the alkoxy radicals in the phosphorus-containing reactants, thus the two alkoxy radicals in the dialkylphosphite, for example, is codeterminant of the respective direction of the course of the reaction. Alkoxy radicals with steric inhibition, for example, isooctyl or isopropyl radicals, lead the reaction in the direction toward tetrakis acids, and radicals without steric hindrance, particularly the ethoxy radical, steer the reaction in the direction of tris acids. When the course of the reaction is predetermined, as in the case of vinylidene chloride (toward the tris acid) or in the case of the tetrachloroethylene (toward the tetrakis acid), an influence on the reaction through these measures is eliminated.

There are other applicable factors to be considered regarding process conditions. The amount of tetrahydrofuran is not critical, provided that the adequate miscibility of the reactants is assured. The use of low-viscosity phosphite solutions in the process is especially preferred. The reaction temperature usually is in the range of from about −20° C. to 100° C., frequently preferably in the range from about 0° to 80° C. When reaction pairs are used that are mutually highly reactive, the cooling of the reaction, at least initially, and the starting at even lower temperatures, for example, at −70° C., may be advantageous. Initial cooling is used, for example, for the reaction of tetrachloroethylene with diethylphosphites or diisopropylphosphites. When, in contrast, slow-reacting reaction partners are used, for example, the combination of vinylidene chloride with diisooctylphosphite, heating of the reaction mixture from the start may be desirable.

The reaction components—both dissolved in anhydrous THF—usually are combined slowly with agitation, while the reaction mixture is cooled or heated. If desired, the reaction is sufficiently continued with agitation or with refluxing. The formation of the desired reaction product can be followed by $^{31}$P-NMR-spectroscopic testing during the course of the reaction.

At least initially, the reaction proceeds under an inert gas and with the exclusion of moisture. However, it has been found in some cases that water can be added after the complete mixing of the reaction components and complete primary reaction of the reaction mixture, to further support the final course of the reaction. In particular an excessively brisk final reaction can also be slowed down by the addition of water.

The addition of water can be advantageous during the completion of the reaction between sodium diethylphosphite and tetrachloroethylene. When water is added to the reaction mixture, the preferred amount is from about 1 to 2 mols of water per mol of olefin.

The use of closed reaction vessels can be useful when working with highly volatile components, for example, vinylidene chloride. The work usually can be carried out under the pressure developed by the reaction and at the reaction temperature.

The primary reaction mixture can be worked up as follows: The reaction mixture is neutralized, that is, its pH is adjusted to a value preferably in the range of approximately 7. For example, a carboxylic acid, especially acetic acid, can be used for this purpose. Also suitable is, for example, a solution of glacial acetic acid in THF (1:1). Subsequently, if necessary after evaporation of the reaction mixture, sodium chloride formed is removed by a known method, for example, by washing with water, filtering, and/or centrifuging.

The oligophosphonic acid esters or oligophosphinic acid esters obtained can be isolated in this form and purified. However, frequently the desired reaction products are not the esters but the free acids or their salts, especially their water-soluble salts. For this purpose the esters can be saponified in a known manner by acid hydrolysis, for example, by heating with aqueous mineral acids such as hydrochloric acid or hydrobromic acid, or pyrolysis. The free acids can be converted into their salts by partial or complete neutralization with inorganic or organic bases.

Polyphosphonic acids are known as excellent sequestering agents for polyvalent metallic ions and are particularly suitable as complexing agents for alkali earth metal ions. Usually they have a characteristic threshold effect. Their practical application in in the technical as well as in the cosmetic and/or pharmaceutical area. Numerous novel polyphosphonic acid compounds with interesting application possibilities are made accessible by the invention. For example, oligophosphinic acids can be used as flame-retardants or for the impregnation of paper. Again, the process according to the invention opens up possibilities for expansion in this field.

The invention is also directed to new oligophosphonic acid derivatives or oligophosphinic acid derivatives that can be prepared by the method according to the invention. An especially important new oligophosphonic acid compound is 1,1,2,2-ethanetetrakisphosphonic acid of the general formula

wherein R' represents hydrogen, and esters and salts thereof. With respect to the esters, R' represents a hydrocarbon radical, preferably an alkyl with from 1 to 8 carbon atoms, and with respect to the salts, water-soluble salts, particularly alkali metal salts, are preferred.

Additional important new oligophosphinic acid compounds comprise 1,1,2-ethane-tris-(alkyl- or arylphosphinic acids) of the general formula

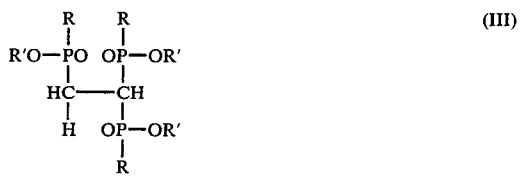

wherein R represents an alkyl, especially with from 1 to 5 carbon atoms and preferably with from 1 to 3 carbon atoms, or an aryl, preferably a phenyl group, and R' represents a hydrogen atom, and esters and salts thereof, as well as the 1,1,2,2-ethane-tetrakis-(alkyl- or arylphosphinic acids) of the general formula

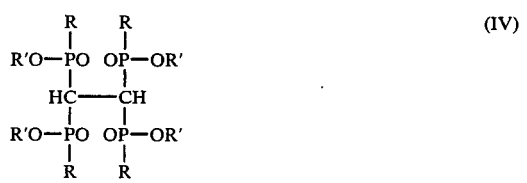

wherein R represents an alkyl, especially with from 1 to 5 carbon atoms and preferably with from 1 to 3 carbon atoms, or an aryl, preferably a phenyl group, and R' represents a hydrogen atom, and esters and salts thereof. With respect to the esters, R' represents a hydrocarbon radical, preferably an alkyl with from 1 to 8 carbon atoms, and with respect to the salts, water-soluble salts, particularly alkali metal salts, are preferred.

The following examples are intended to illustrate the invention and are not to be construed as limiting the invention thereto.

EXAMPLES

Example 1

1,1,2-Ethane-trisphosphonic Acid Hexaethyl Ester from Vinylidene Chloride

Equipment: 4-liter three-neck flask, KPG-agitator, reflux condenser, dropping funnel, and protective nitrogen gas.

A solution of 552 gm (4 mols) of diethylphosphite in 400 ml of abs. THF was added dropwise over a period of 4.5 hours to a suspension of 120 gm (4 mols) of sodium hydride paste (Merck & Co., Inc. 80% NaH in liquid paraffin) in one liter of anhydrous tetrahydrofuran (THF). When the evolution of hydrogen stopped, the mixture was refluxed for one hour, which led to the formation of a clear solution of sodium diethylphosphite. A solution of 192 gm (2 mols) of vinylidene chloride in 100 ml abs. THF was added to this mixture over a period of three hours at the reflux temperature.

The batch was refluxed for another 2.5 days, during which process the reflux condenser was cooled intensely because of the low boiling point of $CH_2=CCl_2$. After cooling, the pH was adjusted to 7 with the addition of glacial acetic acid/THF (1:1), and the entire batch was evaporated in a rotation evaporator. The residue is taken up in 1200 ml of methylene chloride and washed with 1100 ml of water. The separated water phase was again extracted with methylene chloride. The combined methylene chloride phases were dried over sodium sulfate and then evaporated in the rotation evaporator. The liquid paraffin of the sodium hydride paste used initially was removed by shaking the crude ester mixture with ligroin 30–50. Repeated distillation with a thin-layer vaporizer KDL-1 by Leybold-Heraeus produced the colorless 1,1,2-ethane-trisphosphonic acid hexaethyl ester with a boiling point of 194°–196° C. at 0.5 torr.

Yield: 400 gm (68.5% of theory). ($^{31}P$ {$^1H$}NMR showed that the primary yield exceeded 90%.).

EXAMPLE 2

1,1,2-Ethane-trisphosphonic Acid

One hundred nine grams (0.25 mol) of 1,1,2-ethane-trisphosphonic acid hexaethyl ester were refluxed with 500 ml of 48% HBr for four hours. After removal of excess hydrobromic acid in the rotation evaporator, a viscous oil remained, from which the crystalline acid was separated by cooling (in a refrigerator) for several days.

Yield: practically quantitative.

An ester cleavage with 36% HCl took place analogously.

EXAMPLE 3

1,1,2-Ethane-trisphosphonic Acid Hexaethyl Ester from Trichloroethylene

Equipment: 2-Liter three-neck flask, KPG-agitator, dropping funnel, reflux condenser, and protective nitrogen gas.

A solution of 276 gm (2 mols) of diethylphosphite in 500 ml of abs. THF was added dropwise at room temperature to a suspension of 60 gm (2 mols) of sodium hydride paste (Merck & Co., Inc., 80% NaH in liquid paraffin) in 500 ml of anhydrous tetrahydrofuran. When the evolution of hydrogen stopped, the reaction mixture was refluxed for one hour, which led to the formation of a clear solution of sodium diethylphosphite.

A solution of 131 gm (1 mol) of trichloroethylene in 100 ml of abs. THF was added dropwise at room temperature over a period of one hour, and the mixture was then agitated for one hour. After standing overnight, the pH of the reaction mixture was adjusted to 7 with glacial acetic acid/THF (1:1), and the entire batch was subsequently evaporated in the rotation evaporator. After taking up in 500 ml of toluene, the NaCl formed was washed out with water, and the toluene phase was separated and dried with sodium sulfate. After evaporation in the rotation evaporator, the material was distilled in a thin-layer evaporator KDL-1 by Leybold-Heraeus, and 73 gm of a mixture of crude ester and liquid paraffin was obtained. The liquid paraffin was removed by shaking with ligroin 30–50, and after another distillation, 33 gm of 1,1,2-ethane-trisphosphonic acid hexaethyl ester with a boiling point of 194°–196° C. at 0.3 torr were obtained.

Yield: 23% of theory, ($^{31}$P{$^1$H}NMR showed that the primary yield was far greater.).

Example 4

1,1,2,2-Ethane-tetrakisphosphonic Acid Octaethyl Ester from Tetrachloroethylene; 1,1,2,2-Ethane-tetrakisphosphonic Acid Equipment: 2-Liter three-neck flask, KPG-agitator, reflux condenser, dropping funnel, and protective nitrogen gas.

A solution of 138 gm (1 mol) of diethylphosphite in 200 ml of abs. THF was added dropwise to a suspension of 30 gm (1 mol) of sodium hydride paste (Merck & CO., Inc., 80% NaH in liquid paraffin) in 200 ml of anhydrous tetrahydrofuran. When the evolution of hydrogen stopped, the reaction mixture was refluxed for one hour, which led to the formation of a clear solution of sodium diethylphosphite. To this mixture a solution of 66 gm (0.4 mol) of tetrachloroethylene in 80 ml of abs. THF was added dropwise, with ice cooling, over a period of 45 minutes, which resulted in the formation of a fine particle precipitate. When the addition was complete, the mixture was warmed to room temperature, and the suspension formed was agitated vigorously for one hour. Then, a solution of 30 gm of water in 80 ml of THF was added slowly with intensive agitation, which resulted in the development of an intensely red color. The pH was then adjusted to 7 with glacial acetic acid/THF (1:1), and the red color disappeared. The entire batch was then evaporated in the rotation evaporator, the residue was taken up in methylene chloride, and the NaCl formed was removed by washing with water. The methylene chloride phase was separated, dried over sodium sulfate, and again evaporated in the rotation evaporator. The oily residue was then refluxed with 125 ml of 36% HCl for three hours. After the removal of the excess hydrochloric acid, a brown, viscous oil remained, and the liquid paraffin from the sodium hydride paste soon separated on the surface of the oil. The liquid paraffin was removed by shaking with ligroin 30–50. The viscous, oily residue consisted almost quantitatively of 1,1,2,2-ethane-tetrakisphosphonic acid, as shown by $^{31}$P{$^1$H}NMR.

Yield of the pure acid: 34.3%.

Example 5

1,1,2-Ethane-trisphosphonic Acid Hexaisopropyl Ester from Vinylidene Chloride

Equipment: 4-Liter three-neck flask, KPG-agitator, dropping funnel, reflux condenser, and protective nitrogen gas.

A solution of 498 gm (3 mols) of diisopropylphosphite in one liter of abs. THF was added dropwise at room temperature to a suspension of 90 gm (3 mols) of sodium hydride paste (Merck & Co., Inc., 80% NaH in liquid paraffin) in two liters of anhydrous tetrahydrofuran. When the evolution of hydrogen stopped, the mixture was refluxed for one hour and allowed to stand at room temperature overnight. Then, a solution of 97 gm (1 mol) of vinylidene chloride in 250 ml of abs. THF was added directly, and the mixture was refluxed. The reflux condenser was cooled intensely! After a total reflux time of six hours, the entire batch was adjusted to a pH of 7 with glacial acetic acid/THF (1:1) and evaporated in the rotation evaporator. The oily residue was taken up in one liter of methylene chloride, and the NaCl formed was then washed out with one liter of water. After separation and drying of the methylene chloride phase over sodium sulfate, it was evaporated in the rotation evaporator. The crude ester formed was subjected to thin-layer evaporation with the Leybold-Heraeus KDL-1. A quantity of 210 gm of a colorless ester with a boiling point of 220° C. at 0.02 torr was obtained (43% of theory). The distillation must proceed quickly. A slow distillation results in pyrolysis, and 1,1,2-ethane-trisphosphonic acid remains as solid residue.

Example 6

1,1,2,2-Ethane-tetrakisphosphonic Acid Octaisopropyl Ester from Trichloroethylene Equipment: 2-Liter three-neck flask, KPG-agitator, dropping funnel, reflux condenser, and protective nitrogen gas.

(a) 0.5 MM Solution of Sodium Diisopropylphosphite:

A solution of 166 gm (1 mol) of diisopropylphosphite in 250 ml of abs. THF was added dropwise to a suspension of 30 gm (1 mol) of sodium hydride paste (Merck & Co., Inc., 80% NaH in liquid paraffin) in 500 ml of anhydrous tetrahydrofuran at room temperature, over a period of two hours. When the evolution of hydrogen stopped, the mixture was refluxed for 30 minutes and then cooled, and the sodium diisopropylphosphite solution was made up to two liters with abs. THF in a 2-liter measuring flask.

(b) Conversion with Trichloroethylene:

Quantities of 6.5 gm (0.05 mol) of trichloroethylene and 50 ml of abs. THF were placed in a 500 ml three-neck flask. At room temperature, 400 ml of the 0.5M sodium diisopropylphosphite solution from step (a) were added dropwise over a period of one hour. The mixture was refluxed for four hours and then allowed to stand at room temperature overnight, and the pH was then adjusted to 7 with glacial acetic acid/THF (1:1). The entire batch was evaporated in the rotation evaporator and again taken up with 500 ml toluene. The NaCl formed was removed by washing with water, and the toluene phase was separated, dried over sodium sulfate, and evaporated in the rotation evaporator. According to NMR analysis, the remaining residue, a slightly yellow oil, was practically pure 1,1,2,2-ethane-tetrakisoctaisopropyl ester, which cannot be distilled. Yield: practically quantitative.

EXAMPLE 7

1,1,2,2-Ethane-tetrakisphosphonic Acid Octaisopropyl Ester from Tetrachloroethylene The procedure in Example 6 was followed, but with the following changes:

Material in vessel: 8.3 gm (0.05 mol) of tetrachloroethylene 50 ml of abs. THF.

Addition: 400 ml of 0.5M sodium diisopropylphosphite solution in THF.

The working up was analogous to that of Example 6.

Result: According to $^{31}P\{^1H\}$NMR analysis, most quantitative conversion into nondistillable, oily 1,1,2,2-ethane-tetrakisoctaisopropyl ester.

Diisooctylphosphite reacts more slowly but basically in a manner similar to diisopropylphosphite. A viscous, nondistillable 1,1,2,2-ethane-tetrakisphosphonic acid octaisooctyl ester was obtained by corresponding conversion with tetrachloroethylene.

Example 8

1,1,2,2-Ethane-tetrakis-(P-methyl)-phosphinic acid from trichloroethylene

First, by use of a procedure analogous to the preparation of diethylphosphite sodium salt in Example 1, the compound methanephosphonous acid isobutyl ester sodium salt (MPAIBNa) of the formula

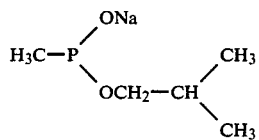

was prepared. In a 2-liter three-neck flask 60 gm (2 mols) of sodium hydride paste (Merck & Co., Inc., 80% of NaH in liquid paraffin) were added to 500 ml of abs. THF. Then a solution of 272 gm (2 mols) of methanephosphonous acid isobutyl ester (MPAIB) in one liter of abs. THF was slowly added dropwise. Thereafter the product was briefly heated with reflux, cooled, and filled up to two liters with abs. THF in a 2-liter measuring flask. The reaction proceeded quantitatively. The solution was stored under nitrogen.

The MPAIBNa thus obtained was then reacted with trichloroethylene to form 1,1,2,2-ethane-tetrakis-(P-methyl)-phosphinic acid:

Initial charge: 33 gm of trichloroethylene (0.25 mol) in 250 ml of abs. THF.

Addition: 920 ml of 1M MPAIBNa solution in THF cooled with ice, over a period of two hours.

Procedure:

After complete addition of the MPAIBNa solution, the mixture was heated for one hour with reflux, cooled to room temperature neutralized with glacial acetic acid to a pH of 7, and concentrated in the rotation evaporator. The oily residue was taken up with methylene and washed NaCl-free with water. After concentration of the phase dried over $MgSO_4$, 139.6 gm of the crude ester mixture remained.

Yield: 93% of theory.

Splitting of the ester with concentrated HCl and isolation of the free acid was effected analogously to Example 2 or 4, respectively. Yield of pure acid 40% (the yield was determined by NMR spectroscopy).

EXAMPLE 9

1,1,2,2-Ethane-tetrakis-(P-methyl)-phosphinic acid from Tetrachloroethylene

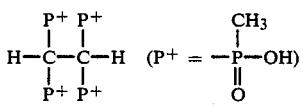

The apparatus was analogous to that of Example 4.

One liter of a 1M MPAIBNa solution was added to a solution of 42.2 gm (0.254 mol) of tetrachloroethylene in 250 ml of abs. THF, with ice bath cooling, over a period of two hours. A spontaneous exothermic reaction was observed with separation of NaCl and increasing brown coloration. After complete addition, the resulting solution was heated for one hour with reflux and was then cooled to room temperature. The pH of the solution was carefully adjusted to a pH of 7 with glacial acetic acid, and then the entire solution was concentrated in the rotation evaporator. The brown viscous oily residue was taken up with methylene chloride and washed repeatedly with water. After drying over magnesium sulfate, the organic phase was again concentrated in the rotation evaporator.

Yield of crude ester mixture: 125.8 gm.

For analytical purposes, 4.5 gm of the ester mixture were distilled in the spherical tube evaporator. The result was 0.9 gm of the by-product methanephosphonic acid diisobutyl ester as well as 3.6 gm of the stereoisomer mixture of 1,1,2,2-ethane-tetrakis-(P-methyl)-phosphinic acid isobutyl ester. The ester mixture not distillable at 95° C./0.05 torr. represented a yield of 71.3% of theory in the first reaction stage.

A quantity of 86.3 gm of the crude ester mixture was heated with 150 ml of conc. HCl for three hours with reflux. After concentration of the reaction mixture in the rotation evaporator, there remained 62.8 gm of a crude acid mixture, which according to NMR findings was 86.2% by weight 1,1,2,2-ethane-(P-methyl)-tetrakis-phosphinic acid. By addition of methanol the tetrakis-phosphinic acid was precipitated, which precipitate can be purified by further washing with methanol. After drying over phosphorus pentoxide, 21 gm (35.6%) of the colorless acid remained.

$^{31}P\{^1H\}$NMR showed this to be a pure product, $\delta_p$ of a 1M solution in KOD=38.8 ppm.

Example 10

1,1,2,-Ethane-tris-(P-methyl)-phosphinic acid from Vinylidene chloride

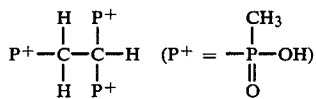

In a 4-liter three-neck flask with reflux condenser, KPG agitator, inside thermometer, dropping funnel and $N_2$ shielding gas inlet, one liter of a 4M solution of methane-phosphonous acid isobutyl ester in abs. THF was added dropwise to a suspension of 120 gm (4 mols) of sodium hydride paste (Merck & Co., Inc., 80% in liquid paraffin), over a period of 2.5 hours. Then the solution was briefly heated with reflux until a clear solution resulted.

During a period of 3.5 hours, 130 ml (1.3 mols) of vinylidene chloride, dissolved in 370 ml of abs. THF, were added dropwise at −5° C. (ice/NaCl) to the cooled solution of MPAIBNa. After complete addition, stirring was continued for another two hours at room temperature. After the mixture stood overnight, the product was neutralized with a 6M solution of glacial acetic acid in THF; also, 40 ml of water were added. The flocculated precipitate (NaCl) was filtered off and washed with THF. The combined organic phases were concentrated in the rotation evaporator after drying over magnesium sulfate, leaving 555 gm of a crude ester mixture. Separation by short-path distillation (KDL-4)

provided at 56° C./0.01 torr at first 119 gm of methane-phosphonic acid diisobutyl ester, then at 130° C./0.001 torr to 160° C./0.06 torr a colorless product solidifying like a wax: 195 gm of an isomer mixture of 1,1-ethane-bis-(P-methyl)-phosphinic acid isobutyl ester (39%) and 1,1,2-ethane-tris-(P-methyl)-phosphinic acid isobutyl ester (61%). The distillation residue comprised 240 gm of an isomer mixture in the ratio of 14:86. The 1,2-ethane-bis-(P-methyl)-phosphinic acid obtained as by-product in the first fraction was identified by comparison with authentic samples.

Two hundred forty grams of the residue obtained were heated with reflux for five hours with 300 ml of conc. HCl and then concentrated in the rotation evaporator. Recrystallization from methanol/acetone led to the tris-phosphinic acid, a colorless compound.

$^{31}P\{^1H\}$NMR in KOD showed an $AB_2$-system of the pure substance at $\delta_{PA}=43.5$ ppm, $\delta_{PB}=39.2$ ppm, $J_{AB}=16$ Hz.

Yield: 40.1 gm (39% of theory).

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. The compound of the formula

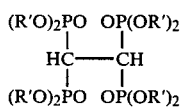

wherein R' represents an alkyl with up to 25 carbon atoms, or water-soluble salt thereof.

2. The compound of the formula

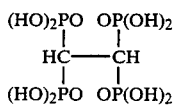

or a water-soluble salt thereof.

3. The compound of the formula

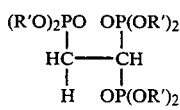

wherein R' represents an alkyl with up to 25 carbon atoms, or a water-soluble salt thereof.

4. The compound of the formula

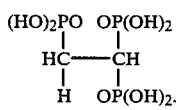

5. A process for preparing an oligophosphonic acid ester which comprises reacting an olefin polyhalide of the formula

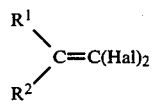

wherein $R^1$ and $R^2$, which may be the same or different, each represent a hydrogen or halogen, with the proviso that at least one of $R^1$ and $R^2$ represents a halogen atom, and Hal represents a halogen atom, with an alkali metal diester of phosphorous acid of the formula (R'O)₂POMe wherein R' is an alkyl radical having up to 25 carbon atoms and Me is an alkali metal, in the presence of a solvent which facilitates exchange of the halogen atoms at the double bond of the olefin polyhalide and saturation of the double bond, the alkali metal diester being added in an excess of the amount stoichiometrically required for exchange of the halogen atoms located at the double bond of the olefin polyhalide and the reaction being carried out at temperatures of from about −20° to 100° C. and, at least initially, in the absence of moisture and under inert gas, to produce a compound of the formula

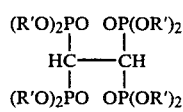

wherein R' is as defined above.

6. The process of claim 5, wherein the solvent is an ether or a tertiary amine compound that is liquid under the reaction conditions.

7. The process of claim 6, wherein the solvent is tetrahydrofuran or methyl-tert.butyl-ether.

8. The process of claim 5, wherein chlorine and/or bromine are present as halogen atoms in the olefin polyhalide.

9. The process of claim 8, wherein the halogen atoms are chlorine atoms.

10. The process of claim 9, wherein the olefin polyhalide is trichloroethylene or tetrachloroethylene.

11. The process of claim 5, wherein the alkali metal diester comprises linear or branched alkyl moieties having up to 20 carbon atoms.

12. The process of claim 11, wherein the alkyl moieties are other than tert.butyl radicals.

13. The process of claim 5, wherein the olefin polyhalide is tetrachloroethylene and the product is an ester of 1,1,2,2-ethane-tetrakisphosphonic acid.

14. The process of claim 5, wherein the olefin polyhalide is trichloroethylene and the product is an ester of 1,1,2,2-ethane-tetrakisphosphonic acid.

15. A process for preparing an oligophosphonic acid which comprises the steps of:

(a) reacting an olefin polyhalide of the formula

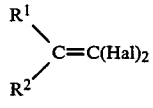

wherein $R^1$ and $R^2$, which may be the same or different, each represent a hydrogen or halogen atom, with the proviso that at least one of $R^1$ and $R^2$ represents a halogen atom, and Hal represents a halogen atom, with an alkali metal diester of phosphorous acid of the formula (R'O)$_2$POMe wherein R' is an alkyl radical having up to 25 carbon atoms and Me is an alkali metal, in the presence of a solvent which facilitates exchange of the halogen atoms at the double bond of the olefin polyhalide and saturation of the double bond, the alkali metal diester being added in an excess of the amount stoichoimetrically required for exchange of the halogen atoms located at the double bond of the olefin polyhalide and the reaction being carried out at temperatures of from about $-20°$ to $100°$ C. and, at least initially, in the absence of moisture and under inert gas, to form a compound of the formula $$\begin{array}{cc}(R'O)_2PO & OP(OR')_2 \\ | & | \\ HC\!\!-\!\!\!-\!\!CH \\ | & | \\ (R'O)_2PO & OP(OR')_2 \end{array}$$

wherein R' is as defined above; and
(b) saponifying the product of step (a) to produce a compound of the formula $$\begin{array}{cc}(HO)_2PO & OP(OH)_2 \\ | & | \\ HC\!\!-\!\!\!-\!\!CH \\ | & | \\ (HO)_2PO & OP(OH)_2 \end{array}.$$

16. The process of claim 15, wherein the solvent is an ether or a tertiary amine compound that is liquid under the reaction conditions.

17. The process of claim 16, wherein the solvent is tetrahydrofuran or methyl-tert.butyl-ether.

18. The process of claim 15, wherein chlorine and/or bromine are present as halogen atoms in the olefin polyhalide.

19. The process of claim 18, wherein the halogen atoms are chlorine atoms.

20. The process of claim 19, wherein the olefin polyhalide is trichloroethylene or tetrachloroethylene.

21. The process of claim 20, wherein the olefin polyhalide is trichloroethylene.

22. The process of claim 20, wherein the olefin polyhalide is tetrachloroethylene.

23. The process of claim 15, wherein the alkali metal diester is added in an excess of approximately 1 mol of alkali metal diester per mol of olefin polyhalide.

24. The process of claim 15, wherein the alkali metal diester comprises linear or branched alkyl moieties having up to 20 carbon atoms.

25. The process of claim 24, wherein the alkyl moieties are other than tert.butyl moieties.

26. A process for preparing an oligophosphonic acid ester which comprises reacting an olefin polyhalide of the formula $$\begin{array}{c}R^1 \\ \diagdown \\ \phantom{R^2}C\!\!=\!\!C(Hal)_2 \\ \diagup \\ R^2 \end{array}$$

wherein $R^1$ and $R^2$, which may be the same or different, each represent a hydrogen or halogen, with the proviso that only one of $R^1$ and $R^2$ may represent a halogen atom, and Hal represents a halogen atom, with an alkali metal diester of phosphorus acid of the formula (R'O)$_2$POMe wherein R' is an alkyl radical having up to 25 carbon atoms and Me is an alkali metal, in the presence of a solvent which facilitates exchange of the halogen atoms at the double bond of the olefin polyhalide and saturation of the double bond, the alkali metal diester being added in an excess of the amount stoichiometrically required for exchange of the halogen atoms located at the double bond of the olefin polyhalide and the reaction being carried out at temperatures of from about $-20°$ to $100°$ C. and, at least initially, in the absence of moisture and under inert gas, to produce a compound of the formula $$\begin{array}{cc}(R'O)_2PO & OP(OR')_2 \\ | & | \\ HC\!\!-\!\!\!-\!\!CH \\ | & | \\ H & OP(OR')_2 \end{array}$$

wherein R' is as defined above.

27. The process of claim 26, wherein the solvent is an ether or a tertiary amine compound that is liquid under the reaction conditions.

28. The process of claim 27, wherein the solvent is tetrahydrofuran or methyl-tert.butyl-ether.

29. The process of claim 26, wherein chlorine and/or bromine are present as halogen atoms in the olefin polyhalide.

30. The process of claim 29, wherein the halogen atoms are chlorine atoms.

31. The process of claim 30, wherein the olefin polyhalide is vinylidene chloride or trichloroethylene.

32. The process of claim 26, wherein the alkali metal diester comprises linear or branched alkyl moieties having up to 20 carbon atoms.

33. The process of claim 32, wherein the alkyl moieties are other than tert.butyl radicals.

34. The process of claim 26, wherein the olefin polyhalide is vinylidene chloride and the product is an ester of 1,1,2-ethane-trisphosphonic acid.

35. The process of claim 26, wherein the olefin polyhalide is trichloroethylene and the product is an ester of 1,1,2-ethane-trisphosphonic acid.

36. A process for preparing an oligophosphonic acid which comprises the steps of:
(a) reacting an olefin polyhalide of the formula $$\begin{array}{c}R^1 \\ \diagdown \\ \phantom{R^2}C\!\!=\!\!C(Hal)_2 \\ \diagup \\ R^2 \end{array}$$

wherein $R^1$ and $R^2$, which may be the same or different, each represent a hydrogen or halogen atom, with the proviso that only one of $R^1$ and $R^2$ may represent a halogen atom, and Hal represents a halogen atom, with an alkali metal diester of phosphorous acid of the formula (R'O)$_2$POMe wherein R' is an alkyl radical having up to 25 carbon atoms and Me is an alkali metal, in the presence of a solvent which facilitates exchange of the halogen atoms at the double bond of the olefin polyhalide and saturation of the double bond, the alkali metal diester being added in an excess of the amount stoichoimetrically required for exchange of the halogen atoms located at the double bond of the olefin polyhalide and the reaction being carried out at temperatures of from about $-20°$ to $100°$ C. and, at least initially, in the absence of moisture and under inert gas, to form a compound of the formula

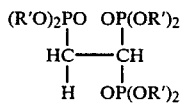

wherein R' is as defined above; and (b) saponifying the product of step (a) to produce a compound of the formula

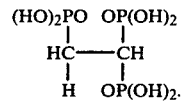

37. The process of claim 36, wherein the solvent is an ether or a tertiary amine compound that is liquid under the reaction conditions.

38. The process of claim 37, wherein the solvent is tetrahydrofuran or methyl-tert.butyl-ether.

39. The process of claim 36, wherein chlorine and/or bromine are present as halogen atoms in the olefin polyhalide.

40. The process of claim 39, wherein the halogen atoms are chlorine atoms.

41. The process of claim 40, wherein the olefin polyhalide is vinylidene chloride or trichloroethylene.

42. The process of claim 41, wherein the olefin polyhalide is vinylidene chloride.

43. The process of claim 41, wherein the olefin polyhalide is trichloroethylene.

44. The process of claim 36, wherein the alkali metal diester is added in an excess of approximately 1 mol of alkali metal diester per mol of olefin polyhalide.

45. The process of claim 36, wherein the alkali metal diester comprises linear or branched alkyl moieties having up to 20 carbon atoms.

46. The process of claim 45, wherein the alkyl moieties are other than tert.butyl moieties.

* * * * *